United States Patent
Duda et al.

(10) Patent No.: US 11,399,803 B2
(45) Date of Patent: Aug. 2, 2022

(54) ULTRASOUND IMAGING SYSTEM AND METHOD

(71) Applicant: General Electric Company, Schenectady, NY (US)

(72) Inventors: Walter Duda, Zipf (AT); Klaus Pintoffl, Grax (AT); Simon Scharinger, Pramet (AT)

(73) Assignee: General Electric Company, Schenectady, NY (US)

( * ) Notice: Subject to any disclaimer, the term of this patent is extended or adjusted under 35 U.S.C. 154(b) by 473 days.

(21) Appl. No.: 16/058,723

(22) Filed: Aug. 8, 2018

(65) Prior Publication Data

US 2020/0046321 A1 Feb. 13, 2020

(51) Int. Cl.
*A61B 8/00* (2006.01)
*G06F 3/041* (2006.01)
*G06F 3/0488* (2022.01)

(52) U.S. Cl.
CPC ............ *A61B 8/467* (2013.01); *A61B 8/4405* (2013.01); *A61B 8/4427* (2013.01); *A61B 8/56* (2013.01); *G06F 3/0416* (2013.01); *G06F 3/0488* (2013.01)

(58) Field of Classification Search
CPC ......... A61B 8/467; A61B 8/56; A61B 8/4405; A61B 8/4427; A61B 8/54; A61B 8/488; A61B 8/485; A61B 8/465; A61B 8/462; A61B 8/469; A61B 8/468; A61B 8/461; A61B 8/463; A61B 8/06; A61B 8/00; G06F 3/0416; G06F 3/0488; G06F 3/041
See application file for complete search history.

(56) References Cited

U.S. PATENT DOCUMENTS

| | | | | |
|---|---|---|---|---|
| 5,889,524 A | * | 3/1999 | Sheehan | G06T 17/20 345/419 |
| 2010/0049050 A1 | * | 2/2010 | Pelissier | A61B 8/00 600/443 |
| 2011/0054266 A1 | * | 3/2011 | Dinino | A61B 8/00 600/300 |
| 2011/0196235 A1 | * | 8/2011 | Dunbar | G16H 40/63 600/437 |
| 2011/0208052 A1 | * | 8/2011 | Entrekin | A61B 8/465 600/437 |
| 2013/0345563 A1 | * | 12/2013 | Stuebe | G01S 7/52074 600/440 |

(Continued)

OTHER PUBLICATIONS

Mishal Safwan, "Emphysematous Cholecystitis: A Deadly Twist to a Common Disease", 2016 (Year: 2016).*

*Primary Examiner* — Amanda Lauritzen Moher
*Assistant Examiner* — Brooke Lyn Klein (57) ABSTRACT

A method and ultrasound imaging system includes displaying a plurality of steps of a workflow on a touchscreen, graphically indicating one of the plurality of steps in the workflow, displaying a text instruction describing the one of the steps in the workflow on the touchscreen at the same time as displaying the plurality of steps, and displaying an ultrasound image on the main display at the same time as displaying the plurality of steps and the text description on the touchscreen. The method and system includes implementing the step described in the text instruction on the ultrasound image displayed on a main display.

13 Claims, 8 Drawing Sheets

(56) References Cited

U.S. PATENT DOCUMENTS

| | | | |
|---|---|---|---|
| 2014/0052000 A1* | 2/2014 | Buckton | A61B 8/0866 600/440 |
| 2015/0038846 A1* | 2/2015 | Abe | A61B 8/06 600/443 |
| 2016/0081659 A1* | 3/2016 | Perrey | A61B 8/463 600/449 |
| 2016/0113631 A1* | 4/2016 | Chono | A61B 8/488 600/441 |
| 2016/0328998 A1* | 11/2016 | Pedersen | A61B 8/4254 |
| 2017/0055952 A1* | 3/2017 | Eskandari | A61B 8/467 |
| 2017/0231601 A1* | 8/2017 | Chono | A61B 8/486 382/128 |
| 2017/0249532 A1* | 8/2017 | Okazaki | G06K 9/481 |
| 2019/0269384 A1* | 9/2019 | Lundberg | A61B 8/463 |
| 2020/0205772 A1* | 7/2020 | Zou | A61B 8/523 |
| 2020/0297775 A1* | 9/2020 | Srivastava | C12N 15/64 |

\* cited by examiner

ULTRASOUND IMAGING SYSTEM AND METHOD

FIELD OF THE INVENTION

This disclosure relates generally to an ultrasound imaging system with a main display and a touchscreen, and a method for displaying both a workflow including a plurality of steps and a text description of one of the steps on the touchscreen at the same time as displaying an ultrasound image on the main display.

BACKGROUND OF THE INVENTION

Ultrasound workflows typically involve a plurality of discrete steps. The steps may include acquiring an ultrasound image of a particular view and/or performing various operations with respect to one or more ultrasound images. For example, steps of conventional ultrasound workflows may involve acquiring an ultrasound image of a specific view, identifying a contour of a specific anatomical region in one or more ultrasound images, positioning an M-mode line, positioning a Doppler gate, identifying a location of a specific portion of a cardiac cycle in a M-mode trace, or identifying an ultrasound frame associated with a particular physiological phase. It may be challenging for a user, particularly when the user is relatively new and/or inexperienced, to accurately implement each of the steps required in order to complete the workflow. It takes an experienced ultrasound operator in order to acquire the correct views in the order required by the workflow. Additionally, according to conventional techniques, a skilled operator may also be required to accurately perform any additional steps required by the workflow.

For at least the reasons described above, there is a need for an improved ultrasound imaging system and method for displaying a workflow.

BRIEF DESCRIPTION OF THE INVENTION

The above-mentioned shortcomings, disadvantages and problems are addressed herein which will be understood by reading and understanding the following specification.

In an embodiment, a method of ultrasound imaging performed with an ultrasound imaging system including both a touchscreen and a main display includes displaying a plurality of steps of a workflow on the touchscreen, graphically indicating one of the plurality of steps in the workflow, and displaying a text instruction describing one of the steps in the workflow on the touchscreen at the same time as displaying the plurality of steps. The method includes displaying an ultrasound image on the main display at the same time as displaying both the plurality of steps and the text description on the touchscreen and implementing the step described in the text instruction on the ultrasound image displayed on the main display.

In an embodiment, an ultrasound imaging system includes an ultrasound probe, a touchscreen configured to receive touch inputs and display at least one of an image and a graphical user interface, a main display configured to display an ultrasound image acquired with the ultrasound probe, and a processor connected to the ultrasound probe, the touchscreen and the main display. The processor is configured to display a plurality of steps of a workflow on the touchscreen, graphically indicate one of the plurality of steps in the workflow, display a text instruction describing one of the steps in the workflow on the touchscreen at the same time as displaying the plurality of steps, and display an ultrasound image on the main display at the same time as displaying the plurality of steps and the text instruction on the touchscreen.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
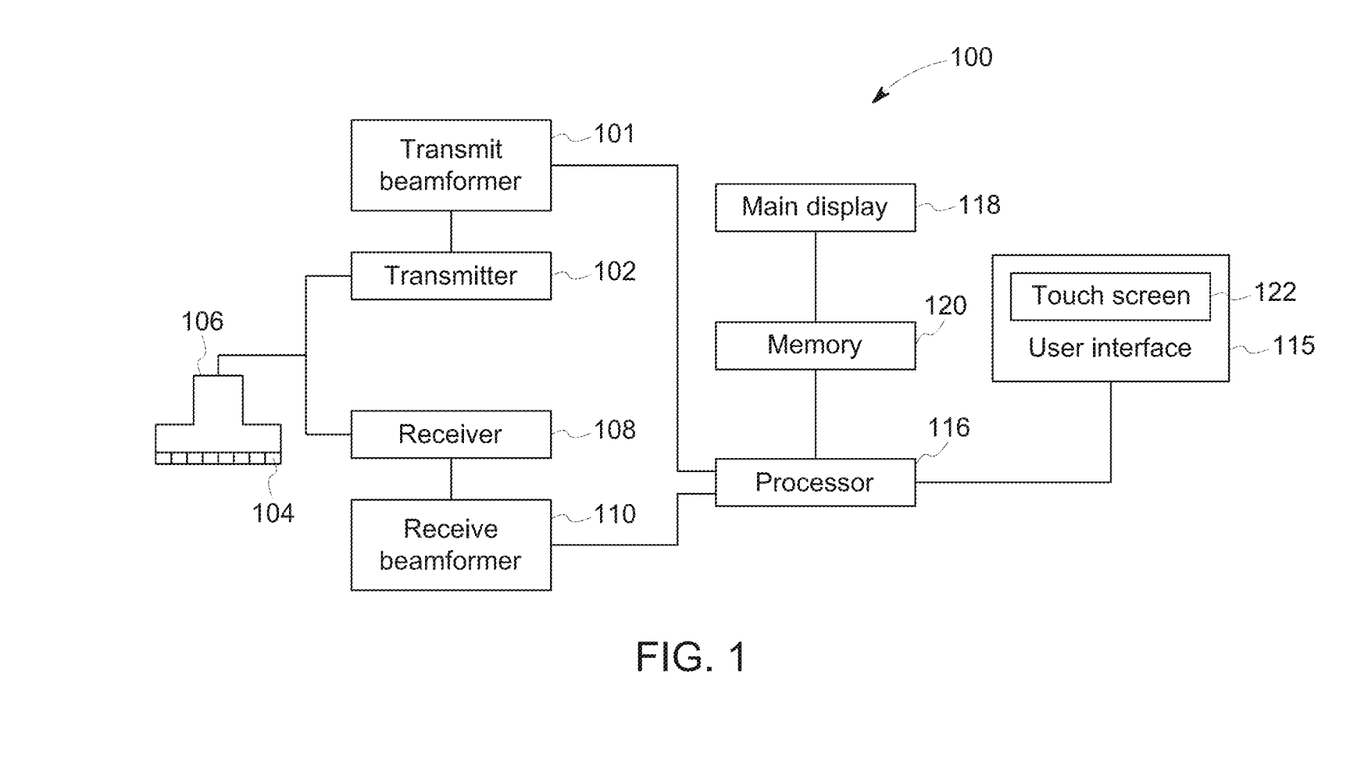
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within a ultrasound probe 106 to emit pulsed ultrasonic signals into a body (not shown). The ultrasound probe 106 may be any type of probe, including a linear probe, a curved array probe, a 1.25D array, a 1.5D array, a 1.75D array, or 2D array probe according to various embodiments. The ultrasound probe 106 may also be a mechanical probe, such as a mechanical 4D probe or a hybrid probe according to other embodiments. The ultrasound probe 106 may be used to acquire 4D ultrasound data that contains information about how a volume changes over time. Each of the volumes may include a plurality of 2D images or slices. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include a one or more user input devices such as a keyboard, hard keys, a touch pad, a track ball, rotary controls, sliders, soft keys, or any other user input devices. The user interface 115 contains a touchscreen 122 according to an exemplary embodiment. The touchscreen 122 may, for instance, be positioned below the main display 118. The touchscreen 122 is configured to receive touch and/or multi-touch inputs from a user. The processor 116 is configured to convert touch inputs received at the touchscreen 122 into operational commands. The touchscreen 122 may be configured to display at least one of an image and a graphical user interface. According to an embodiment, the touchscreen 122 may be positioned so it is easier to reach for a user. For example, the angle and the height of the touchscreen 122 may be different than the main display 118. According to some embodiments, the touchscreen may be configured to show an image in addition to or in place of a graphical user interface. For example, the touchscreen may be configured to display a version of the image displayed on the main display 118. According to some embodiments, the image displayed on the touchscreen 122 may be a smaller version of the image displayed on the main display 118.

The ultrasound imaging system 100 also includes a processor 116 to control the transmit beamformer 101, the transmitter 102, the receiver 108 and the receive beamformer 110. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB).

The processor 116 is in electronic communication with the ultrasound probe 106. The processor 116 may control the ultrasound probe 106 to acquire ultrasound data. The processor 116 controls which of the elements 104 are active and the shape of a beam emitted from the ultrasound probe 106. The processor 116 is also in electronic communication with a main display 118, and the processor 116 may process the ultrasound data into images for display on the main display 118. For purposes of this disclosure, the term "electronic communication" may be defined to include both wired and wireless connections. The processor 116 may include a central processing unit (CPU) according to an embodiment. According to other embodiments, the processor 116 may include other electronic components capable of carrying out processing functions, such as a digital signal processor, a field-programmable gate array (FPGA), a graphics processing unit (GPU) or any other type of processor. According to other embodiments, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame or volume rates may vary based on the size of the region or volume from which data is acquired and the specific parameters used during the acquisition. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to display as an image. It should be appreciated that other embodiments may use a different arrangement of processors. For embodiments where the receive beamformer 110 is a software beamformer, the processing functions attributed to the processor 116 and the software beamformer hereinabove may be performed by a single processor such as the receive beamformer 110 or the processor 116. Or, the processing functions attributed to the processor 116 and the software beamformer may be allocated in a different manner between any number of separate processing components.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending on the size of the volume and the intended application. For example, many applications involve acquiring ultrasound data at a frame rate of 50 Hz. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D images or data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed. The ultrasound imaging system 100 may be a console-based system, a laptop, a handheld or hand-carried system, or any other configuration.

Figure 2:
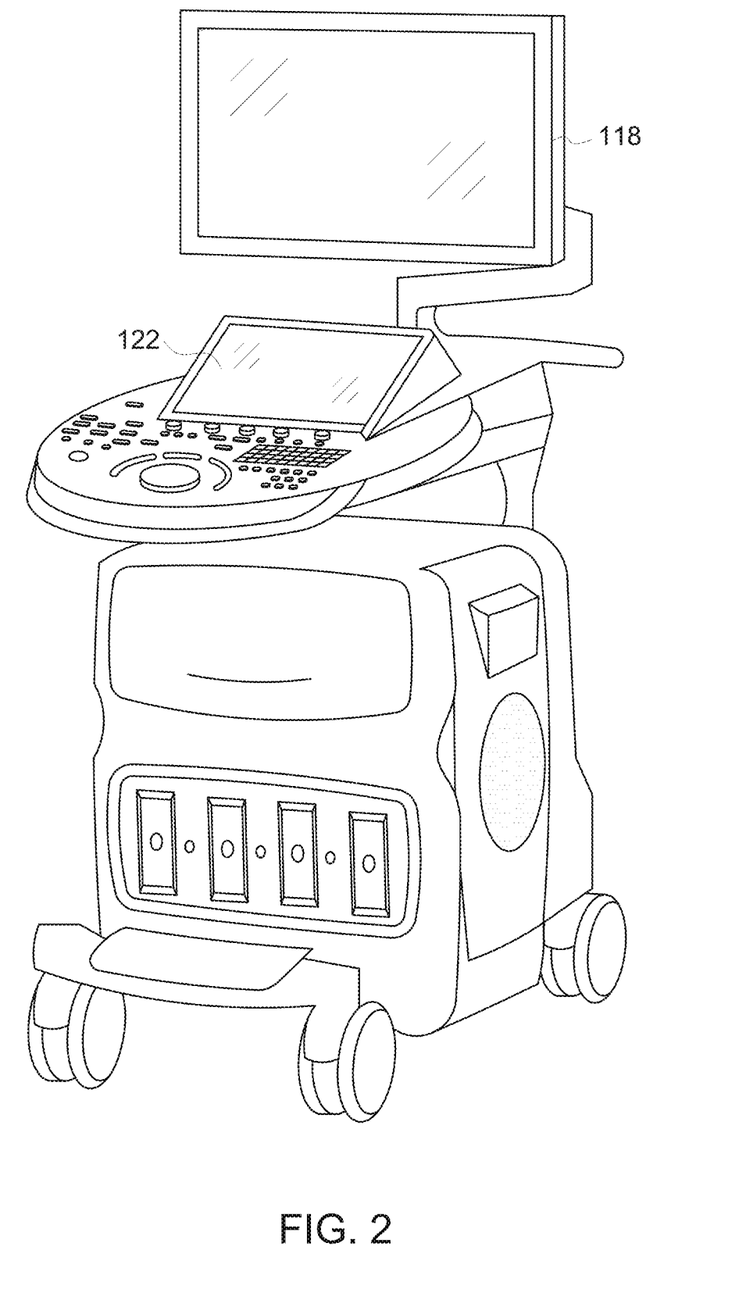
FIG. 2 is schematic representation of an ultrasound imaging system in accordance with an embodiment.

FIG. 2 is an exemplary embodiment of an ultrasound imaging system 100 in accordance with an embodiment. The ultrasound imaging system 100 includes the main display 118 positioned for easy viewing by an operator and the touchscreen 122 positioned below the main display 118. The touchscreen 122 may be disposed at an angle relative to the main display 118 to make it easier for the operator to input touch-based commands and gestures through the touchscreen 122. According to an exemplary embodiment, the main display 118 may be mounted at an angle of 90 degrees to the ground and the touchscreen 122 may be mounted at an angle of 30 degrees to the ground. The main display 118 and the touchscreen may be mounted at different angles according to various embodiments. The angle of the main display 118 and/or the angle of the touchscreen 122 may also be adjustable according to an embodiment.

Figure 3:
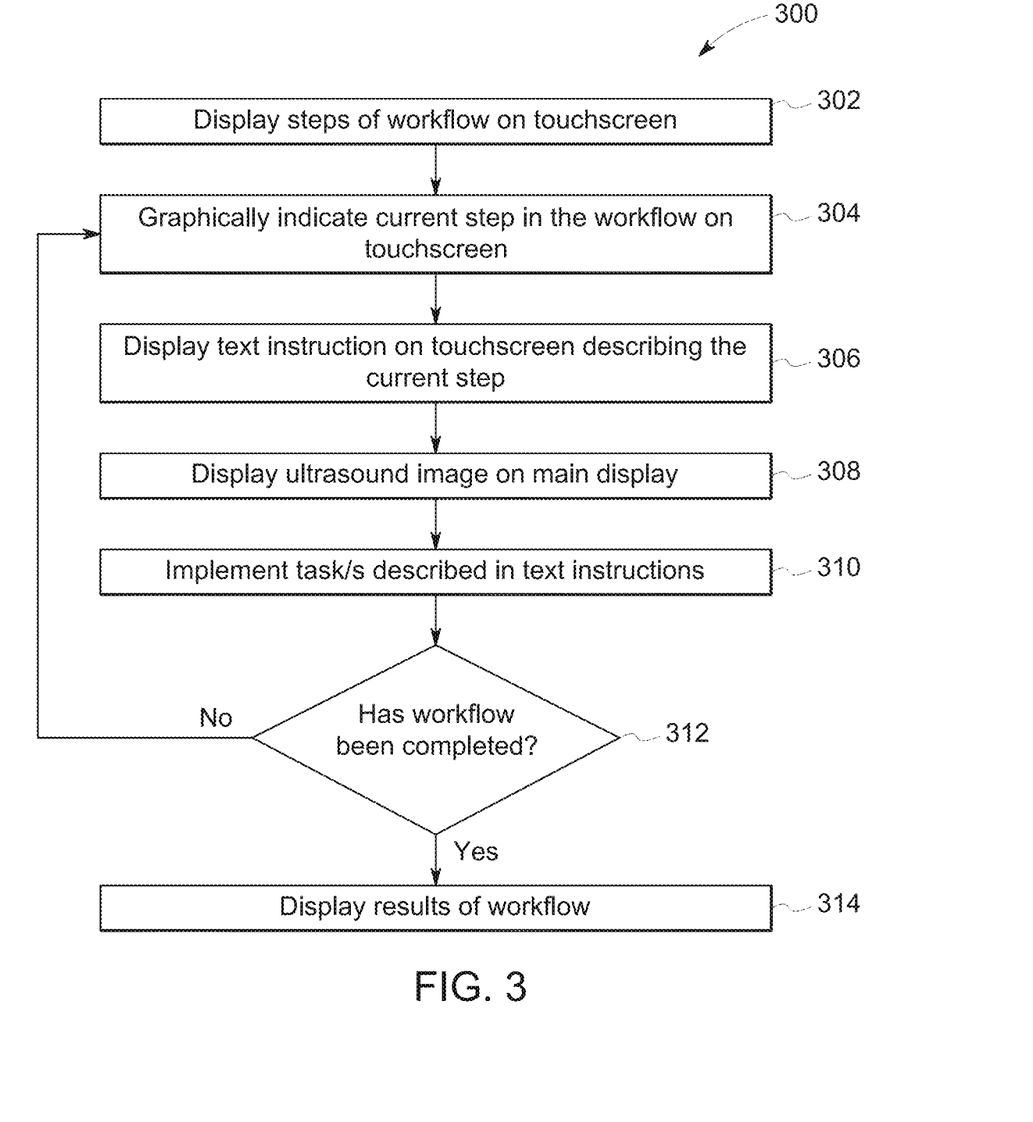
FIG. 3 is a flow chart in accordance with an embodiment.

FIG. 3 is a flow chart of a method 300 in accordance with an exemplary embodiment. The individual blocks of the flow chart represent steps that may be performed in accordance with the method 300. Additional embodiments may perform the steps shown in a different sequence and/or additional embodiments may include additional steps not shown in FIG. 3. The technical effect of the method 300 is the display of both a workflow and a text instruction describing a step of the workflow on a touchscreen at the same time as an ultrasound image is displayed on a main display.

The method 300 will be described in accordance with an exemplary embodiment where the method 300 is performed by the system 100 shown in FIG. 1. Additionally, the method 300 will be described with respect to FIGS. 4, 5, 6, 7, and 8. FIGS. 4, 5, 6, 7, and 8 show exemplary screenshots of the main display 118 and the touchscreen 122 according to an embodiment. In this application, FIGS. 4, 5, 6, 7, and 8 show both a screenshot of the main display 118 and a screenshot of the touchscreen 122. For purposes of the disclosure, the main display 118 is shown above the touchscreen 122. However, it should be understood that the orientation of the main display 118 with respect to the touchscreen 122 may be different in other embodiments. Additionally, in each of FIGS. 4, 5, 6, 7, and 8 it should be appreciated that the screenshot of the main display 118 and the screenshot of the touchscreen 122 both represent the same point in time. FIGS. 4, 5, 6, 7, and 8 will be described in additional detail hereinafter.

Figure 4:
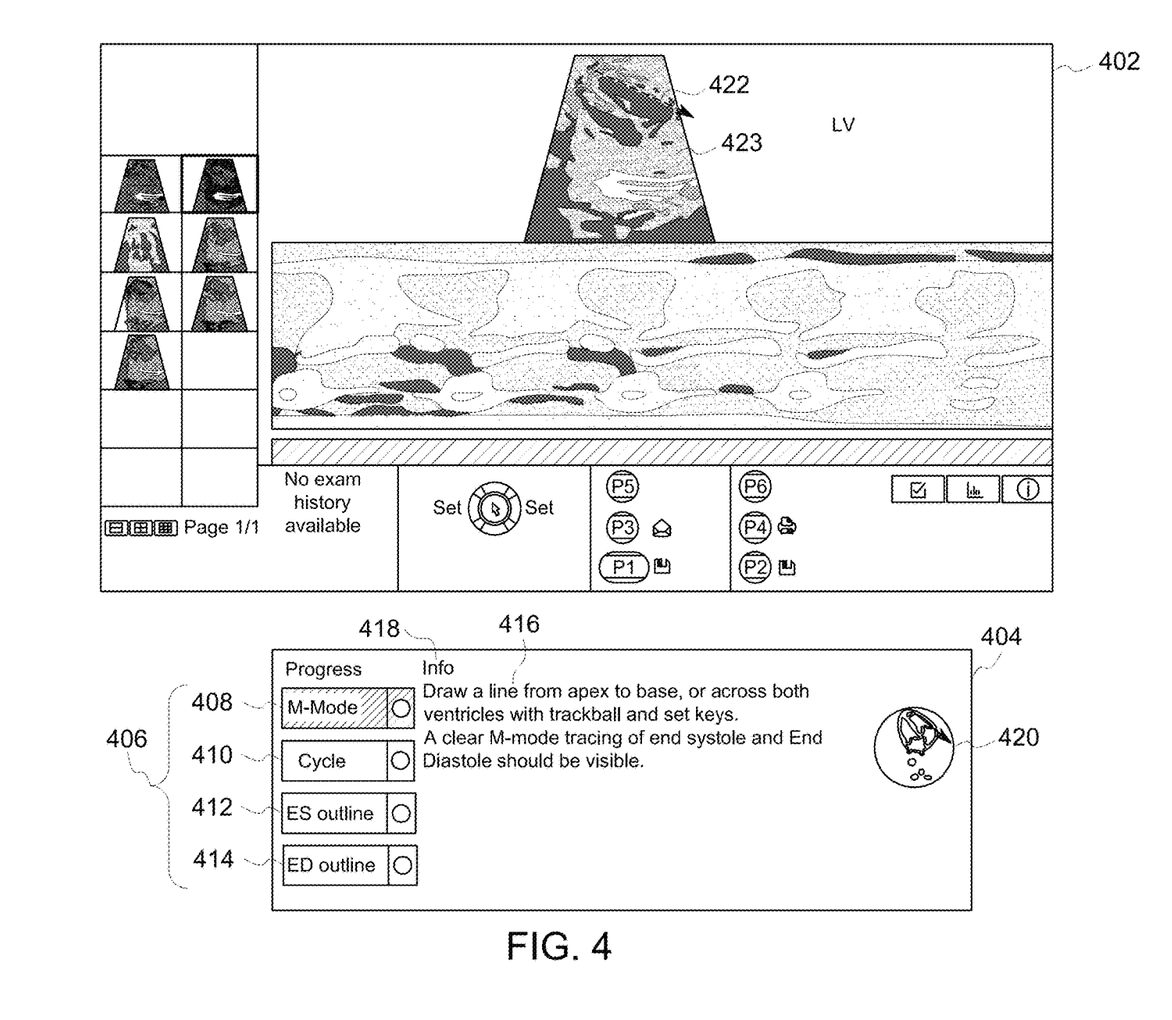
FIG. 4 is a schematic representation of screenshot of a main display and a screenshot of a touchscreen in accordance with an embodiment.

Referring to FIGS. 1, 3 and 4, at step 302, the processor 116 displays steps of a workflow 406 on the touchscreen 122. The method 300 will be described using an exemplary cardiac workflow, but it should be appreciated that different workflows may be used in other embodiments. The exemplary cardiac workflow includes four discrete steps that are displayed on the touchscreen 122. The cardiac workflow includes a first step 408, a second step 410, a third step 412, and a fourth step 414. As shown in the touchscreen screenshot 404, the four steps of the workflow 406 are displayed on the touchscreen 122 by the processor 116.

At step 304, the processor 116 graphically indicates the current step in the workflow 406 on the touchscreen. In the example shown in FIG. 4, the processor 116 has highlighted the first step 408, as shown by the hatching in FIG. 4. It should be appreciated that the processor 116 may use any graphical technique to graphically indicate the current step in the workflow 406. For example, the processor 116 may use any technique to visually differentiate the current step from the other steps in the workflow 406, such as color, transparency, shading, bolding, highlighting, font size, icon size, or one or more icons in order to graphically indicate the current step in the workflow 406. The processor 116 may graphically indicate the current step in the workflow 406, which is the first step 408 according to the embodiment shown in FIG. 4, while all the steps in the workflow 406 are displayed.

At step 306, the processor 116 displays a text instruction 416 on the touchscreen 122 describing the current step in the workflow 406. The text instruction 416 may be identified with a heading 418, such as the word "info" as shown in the exemplary embodiment. The text instruction 416 explains the step or steps that need to be performed by the operator in order to complete the first step 408 of the workflow 406. For example, according to the embodiment shown in FIG. 4, the text instruction 416 indicates that the operator should, "Draw a line from Apex to Base, or across both ventricles with trackball and set keys. A clear M-mode tracing of End Systole and End Diastole should be visible." The text instruction 416 is providing guidance for where the operator should position an M-mode line with respect to various anatomical structures within a patient's heart. According to an exemplary embodiment, the processor 116 may also display a pictogram 420 graphically illustrating the step or steps described by the text instruction 416. In this case, the pictogram 420 shows a schematic illustration of the location where the operator should position the M-mode line with respect to anatomical features in the patient's heart.

At step 308, the processor 118 displays the ultrasound image 423 on the main display 118. According to an embodiment, the ultrasound image 423 on the main display 118 may be acquired in order to implement the operations/tasks described in the text instruction 416. For example, as described previously, the text instruction for the first step 408 according to an embodiment might state: "Draw a line from Apex to Base, or across both ventricles with trackball and set keys. A clear M-mode tracing of End Systole and End Diastole should be visible." In order to implement the text instruction 416, the displayed image, such as the ultrasound image 423, may include a view of a heart showing both ventricles, the apex, and the base.

At step 310, the operator implements the task or tasks described in the text instruction 416. For instance, the operator may use the user interface 115 to position the M-mode line from Apex to Base, or across both ventricles. An exemplary M-mode line 422 is shown on the screenshot of the main display 402. Once the text instruction 416 associated with the first step 408 has been completed, the method 300 advances to step 312.

At step 312, the processor 116 determines if the workflow 406 has been completed. If the workflow 406 has been completed, the method 300 advances to step 314, where the processor 116 displays the results of the workflow 406. Step 314 will be discussed in more detail hereinafter. If the workflow 406 has not been completed, then the method 300 returns to step 304.

Figure 5:
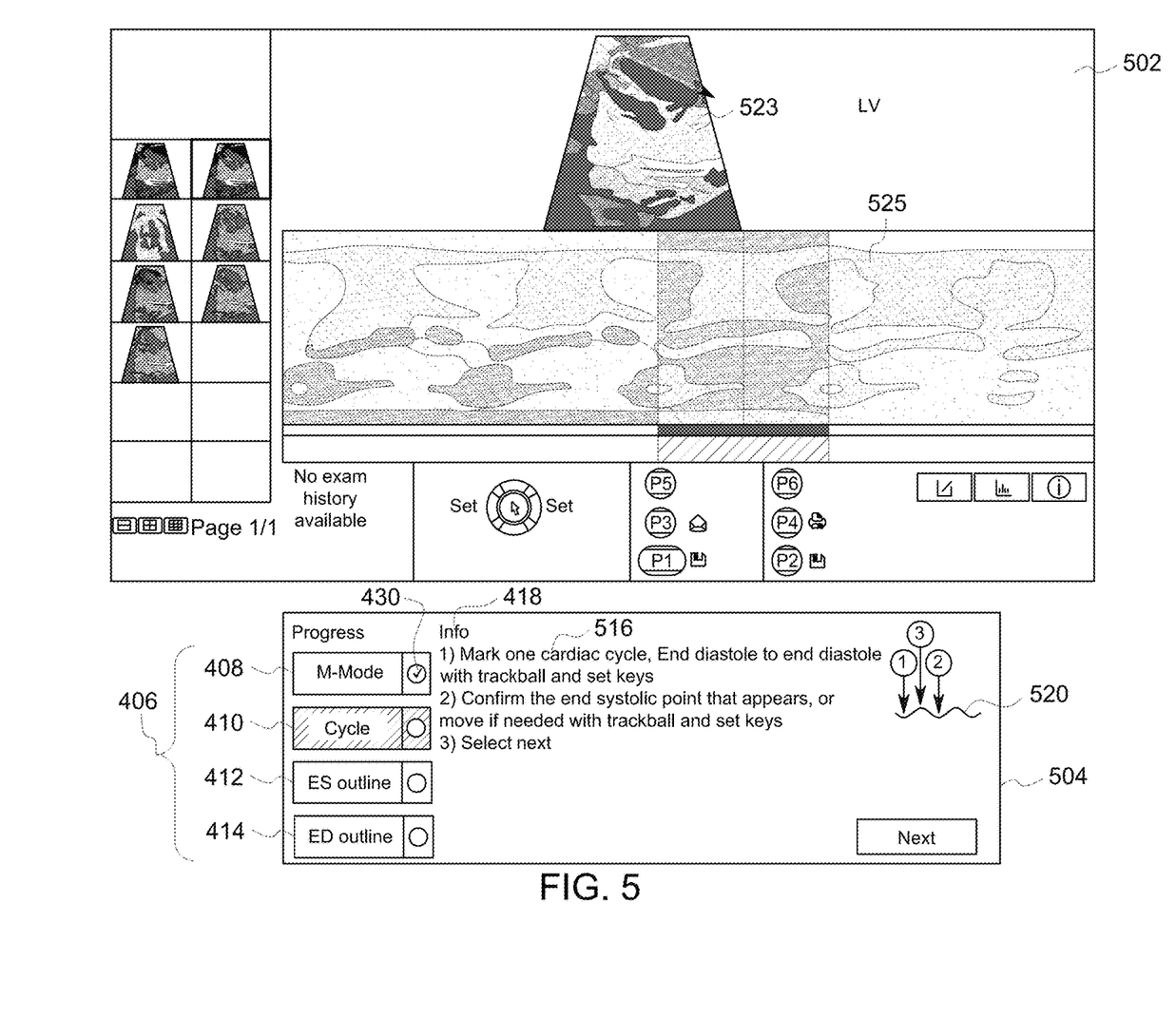
FIG. 5 is a schematic representation of screenshot of a main display and a screenshot of a touchscreen in accordance with an embodiment.

According to an embodiment where the workflow is not completed at step 312, the method 300 returns to step 304. At step 304, the processor 116 graphically indicates the current step in the workflow 406 on the touchscreen 122. For example, according to an embodiment, after the first step 408 has been completed, the processor 116 graphically indicates the second step 410. According to an embodiment, the processor 116 may graphically indicate one or more of the steps in the workflow 406 that have been completed. For example, in the embodiment shown in FIG. 5, the processor 116 displays a first checkmark 430 associated with the first step 408 to indicate that the first step has been completed. FIG. 5 shows a main display screenshot 502 and a touchscreen screenshot 504 in accordance with an embodiment. After completed the first step 408 of the workflow 406, the processor 116 graphically indicates the second step 410 in the workflow at step 304 as shown in FIG. 5. The processor may graphically indicate the second step through highlighting, as indicated by the hatching in FIG. 5. At step 306, the processor 116 displays a text instruction 516 on the touchscreen 122 corresponding to the second step 410. According to the exemplary embodiment shown in FIG. 5, the second step 410 is labeled "Cycle". The text instruction 516 associated with the second step 310 states, "1) Mark one cardiac cycle, End Diastole to End Diastole with Trackball and Set keys 2) Confirm the End Systolic point that appears, or move if needed with trackball and set keys 3) Select Next" The processor 116 may also display a pictogram 520 showing a schematic illustration of the second step 410. For example, the pictogram 520 shows a representation of an M-mode tracing with three points marked on the representation of the M-mode tracing.

At step 308, the processor 116 displays one or more ultrasound images on the main display 118. According to an embodiment, an ultrasound image 523 and an M-mode tracing 525 may be displayed on the main display 118 in order to implement the operations/tasks described in the text instruction 516. The M-mode tracing 525 is an example of a type of ultrasound image according to an embodiment. The ultrasound image 523 may be, for instance, a B-mode image. For example, as described previously, the text instruction for the M-Mode step according to an embodiment might state: "1) Mark one cardiac cycle, End Diastole to end diastole with trackball and set keys 2) Confirm the end systolic point that appears, or move if needed with trackball and set keys 3) Select next" According to this exemplary embodiment, the images displayed on the main display 118 may correspond with the second step 410. For example, the image 502 may include the M-mode tracing 525 upon which the operator may mark one cardiac cycle and confirm the end systolic point as described in the text instruction 516. The processor 116 may implement steps 304, 306, and 308 concurrently so that the current step of the workflow is graphically indicated at the same time as both the text instruction is displayed on the touchscreen and the M-mode tracing is displayed on the main monitor 118.

At step 310, the operator implements the tasks described in the text instructions 516. The operator may use the M-mode tracing 525 to mark one cardiac cycle and to confirm the end systolic point.

At step 312, the processor determines if the workflow 406 has been completed. If the workflow 406 has been completed, the method 300 advances to step 314, where the results of the workflow 406 are displayed. Step 314 will be discussed in more detail hereinafter. If the workflow 406 has not been completed, then the method 300 returns to step 304.

Figure 6:
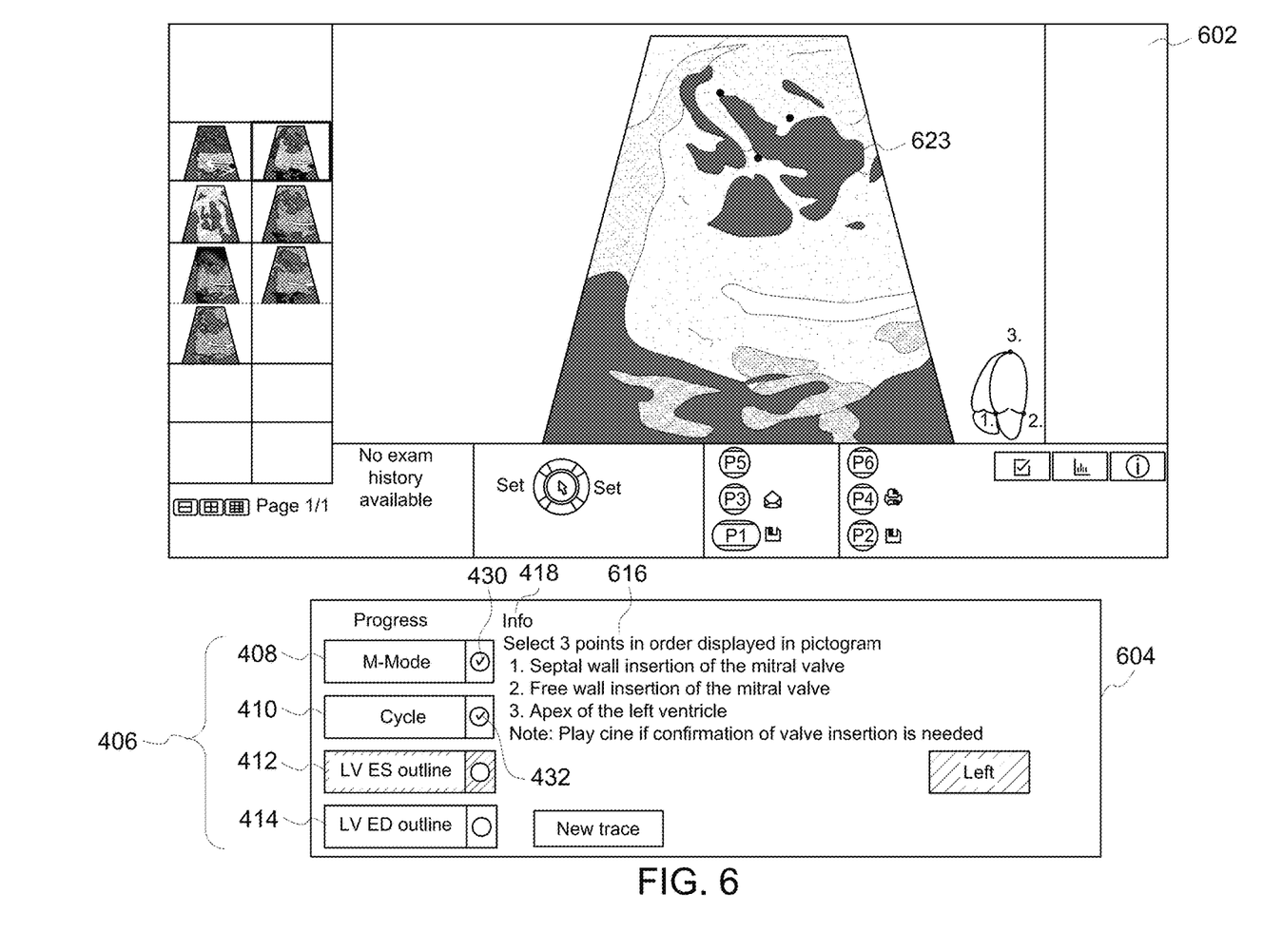
FIG. 6 is a schematic representation of screenshot of a main display and a screenshot of a touchscreen in accordance with an embodiment.

According to an embodiment where the workflow is not completed at step 312, the method 300 returns to step 304. According to an embodiment, the processor 116 may graphically indicate one or more of the steps in the workflow 406 that have been completed. For example, in the embodiment shown in FIG. 6, the processor 116 displays the first checkmark 430 associated with the first step 408 and a second checkmark 432 associated with the second step 410 to indicate that the first step 408 and the second step 410 have been completed. At step 304, the processor 116 graphically indicates the current step in the workflow 406 on the touchscreen 122. For example, according to an embodiment, after the second step 410 has been completed, the processor 116 graphically indicates the third step 412, which may be "LV ES Outline" according to an embodiment. FIG. 6 shows the main display screenshot 602 and the touchscreen screenshot 604 in accordance with an embodiment. After completing the second step 410 of the workflow 406, the processor 116 graphically indicates the third step 412 in the workflow at step 304 as shown in FIG. 6. The processor 116 may graphically indicate the third step 412 by highlighting the third step as indicated by the hatching in FIG. 6. At step 306, the processor 116 displays a text instruction 616 on the touchscreen 122 corresponding to the third step 412. According to the exemplary embodiment shown in FIG. 6, the third step 412 is labeled "LV ES Outline". The text instruction associated with the third step 412 states, "Select 3 points in order displayed in pictogram 1. Septal wall insertion of the mitral valve; 2. Free wall insertion of the mitral valve; 3. Apex of the left ventricle; Note: Play cine if confirmation of valve insertion is needed" according to the exemplary embodiment. A pictogram illustrating the third step is shown in the main display 602.

At step 308, the processor 116 displays an ultrasound image 623 on the main display 118. According to an embodiment, the ultrasound image 602 on the main display 118 may be acquired in order to implement the operations/tasks described in the text instruction 616. The text instruction associated with the third step 412 states, "Select 3 points in order displayed in pictogram 1. Septal wall insertion of the mitral valve; 2. Free wall insertion of the mitral valve; 3. Apex of the left ventricle; Note: Play cine if confirmation of valve insertion is needed" According to this exemplary embodiment, the ultrasound image 623 displayed on the main display 118 may correspond with the third step 412. For example, the ultrasound image 623 may show a left ventricle at end-systole. The processor 116 may implement steps 304, 306, and 308 concurrently so that the current step of the workflow is graphically indicated at the same time as the text instruction 616 is displayed on the touchscreen 122 and the ultrasound image 623 is displayed on the main monitor 118.

At step 310, the operator implements the tasks described in the text instructions 616. The operator may, for instance, select the three points described by text instruction 616.

At step 312, the processor 116 determines if the workflow has been completed. If the workflow has been completed, the method 300 advances to step 314, where the results of the workflow are displayed. Step 314 will be discussed in more detail hereinafter. If the workflow 406 has not been completed, then the method 300 returns to step 304.

Figure 7:
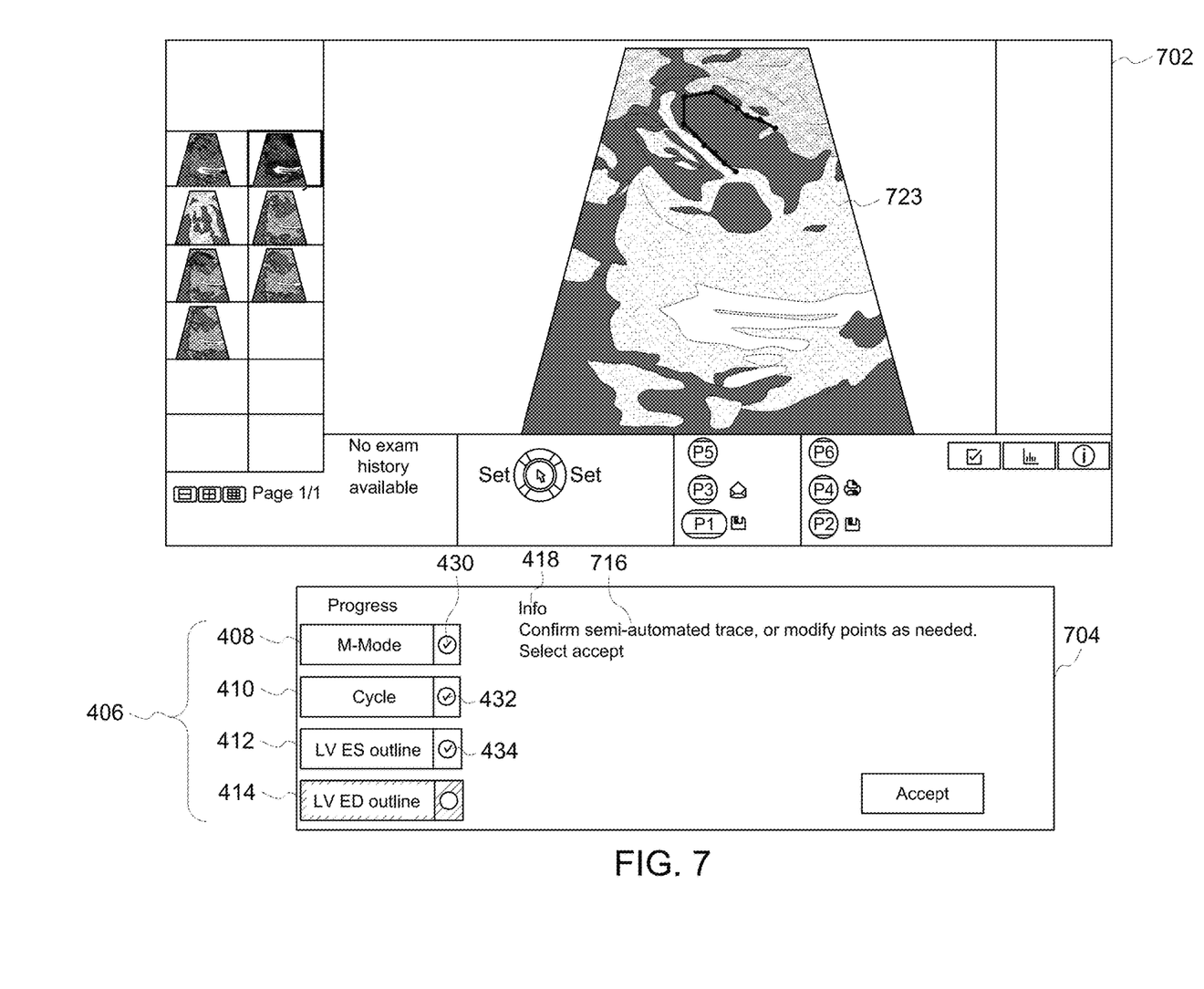
FIG. 7 is a schematic representation of screenshot of a main display and a screenshot of a touchscreen in accordance with an embodiment.

According to an embodiment where the workflow is not completed at step 312, the method 300 returns to step 304. According to an embodiment, the processor 116 may graphically indicate one or more of the steps in the workflow 406 that have been completed. For example, in the embodiment shown in FIG. 7, the processor 116 displays the first checkmark 430 associated with the first step 408, the second checkmark 432 associated with the second step 410, and a third checkmark 434 associated with the third step 412 to indicate that the first step 408, the second step 410, and the third step 412 have been completed. Other embodiments may use a different technique to graphically indicate which of the steps have been completed. For example, other embodiment may use a technique such as color, transparency, shading, bolding, highlighting, font size, icon size, or icons other than a checkmark to graphically indicate that one or more steps in the workflow have been completed. At step 304, the processor 116 graphically indicates the current step in the workflow 406 on the touchscreen 122. For example, according to an embodiment, after the third step 412 has been completed, the processor 116 graphically indicates the fourth step 414, which may be "LV ED Outline" according to an embodiment. FIG. 7 shows the main display screenshot 702 and the touchscreen screenshot 704 in accordance with an embodiment. After completing the third step 412 of the workflow 406, the processor 116 graphically indicates the fourth step 414 in the workflow at step 304. For example, the processor 116 may highlight the fourth step as indicated by hatching in FIG. 7. At step 306, the processor 116 displays a text instruction 716 on the touchscreen 122 corresponding to the fourth step 414. According to the exemplary embodiment shown in FIG. 5, the fourth step 414 is labeled "LV ED outline". The text instruction associated with the fourth step 414 states, "Confirm semi-automated trace, or modify points as needed. Select Accept" according to the exemplary embodiment. While a pictogram illustrating the fourth step is not shown in FIG. 7, according to other embodiments, the processor 116 may show a pictogram illustrating the fourth step 414.

At step 308, the processor 116 displays an ultrasound image 723 on the main display 118. According to an embodiment, the ultrasound image 723 on the main display 118 may be acquired in order to implement the operations/tasks described in the text instruction 716. For example, as described previously, the text instruction for fourth step according to an embodiment might state: "Confirm semi-automated trace, or modify points as needed. Select Accept." According to this exemplary embodiment, the image 702 displayed on the main display 118 may correspond with the fourth step 414. For example, the image 702 may include an ultrasound image showing left ventricle at end-systole. The processor 116 may implement steps 304, 306, and 308 concurrently so that the current step of the workflow is graphically indicated at the same time as both the text instruction is displayed on the touchscreen 122 and the ultrasound image 723 is displayed on the main monitor 118.

At step 310, the operator implements the tasks described in the text instructions. The operator may, for instance, confirm the semi-automated trace or modify points as needed.

Figure 8:
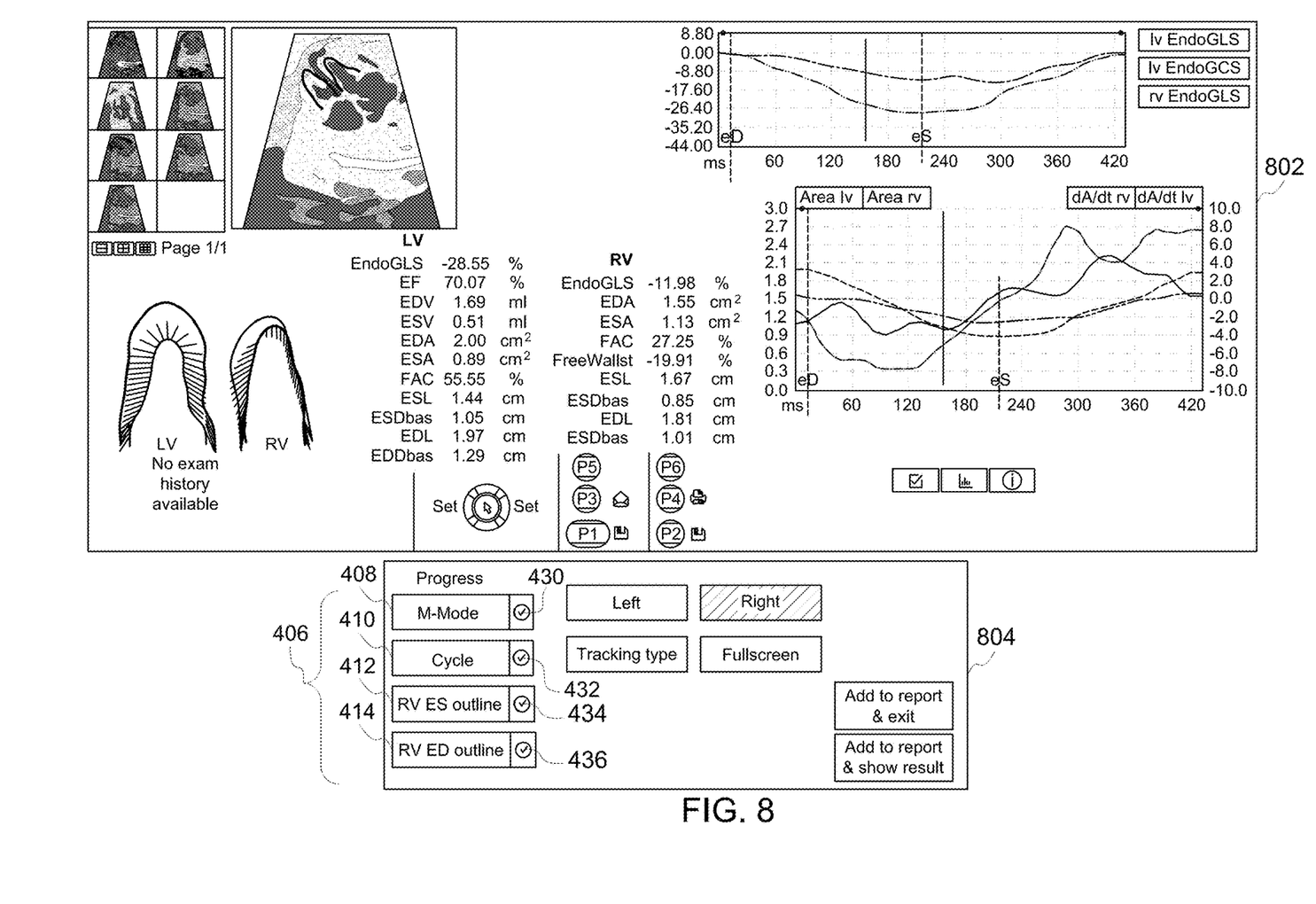
FIG. 8 is a schematic representation of screenshot of a main display and a screenshot of a touchscreen in accordance with an embodiment.

After the workflow 406 has been completed, the method 300 advances to step 314. At step 314, the processor 116 displays the results that are calculated based upon completing the workflow on the main display 802. FIG. 8 is main display screenshot 802 and a touchscreen screenshot 804. For example, according to the exemplary embodiment, the processor 116 may display a plurality of cardiac parameters as the result. For example, the processor 116 may implement one or more algorithms to calculate cardiac parameters based on information either inputted, acquired, or confirmed at steps 408, 410, 412 and 414. The processor 116 may, for example, display parameters such as ejection fraction (EF), end diastolic volume (EDV), end systolic volume (ESV), end diastolic area (EDA), end systolic area (ESA), fractional shortening (FS), fractional area change (FAC), end systolic length (ESL), end systolic basal diameter (ESDbas), end diastolic length (EDL), and end diastolic basal diameter (EDDbas) as shown in screenshot 802. The processor 116 may display other parameters, such as sphericity, according to other embodiments.

While displaying the results (cardiac parameters according to an exemplary embodiment), the processor may display graphs or graphics which correspond to the results displayed on the main display 118. For example, the screenshot of the touchscreen 804 shows that all the steps of the workflow 406 have been completed, as indicated by the checkmarks associated with each of the steps in the workflow. According to an embodiment, the processor 116 may be able to selectively display different sets of parameters. For example, the processor 116 may display a main set of parameters and an advanced set of parameters, where the advanced set of parameters includes more detail or a greater number of parameters than the main set of parameters.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging performed with an ultrasound imaging system including both a touchscreen and a main display, the method comprising:
  displaying a plurality of steps of a workflow on the touchscreen, wherein the plurality of steps includes a first step and a second step;
  graphically indicating the first step in the workflow;
  displaying a first text instruction describing the first step on the touchscreen at the same time as said displaying the plurality of steps;
  displaying a first pictogram graphically illustrating the first text instruction at the same time as said displaying the first text instruction, wherein the first pictogram is displayed on at least one of the touchscreen or the main display, wherein the first pictogram comprises one of a representation of an M-mode tracing with a plurality of points marked on the representation of the M-mode tracing; and displaying an ultrasound image on the main display at the same time as said displaying the plurality of steps on the touchscreen, the first text instruction on the touchscreen, and the first pictogram on at least one of the touchscreen or the main display;

receiving an input of a task described in the first text instruction;

determining that the workflow has not been completed after receiving the input of the task;

graphically indicating the second step in the workflow after determining that the workflow has not been completed;

displaying a second text instruction on the touchscreen describing the second step after determining that the workflow has not been completed;

displaying a second pictogram graphically illustrating the second text instruction at the same time as displaying the second text instruction, wherein the second pictogram is displayed on at least one of the touchscreen or the main display; and displaying an updated ultrasound image on the main display at the same time as said displaying the plurality of steps on the touchscreen, the second text instruction on the touchscreen, and the second pictogram on at least one of the touchscreen or the main display.

2. The method of ultrasound imaging of claim 1, wherein graphically indicating the first step comprises highlighting the first step.

3. The method of ultrasound imaging of claim 1, further comprising graphically indicating that the first step has been completed after said receiving the input of the task described in the first text instruction.

4. The method of ultrasound imaging of claim 1, wherein the workflow is a cardiac workflow.

5. The method of ultrasound imaging of claim 3, wherein said graphically indicating that the first step has been completed comprises displaying a checkmark associated with the first step.

6. The method of ultrasound imaging of claim 4, further comprising determining that the workflow has been completed and automatically calculating a plurality of cardiac parameters after the completion of the workflow.

7. The method of ultrasound imaging of claim 6, wherein the plurality of cardiac parameters includes at least one of end diastolic diameter, end systolic diameter, fractional shortening, and sphericity.

8. An ultrasound imaging system comprising:
an ultrasound probe;
a touchscreen configured to receive touch inputs and display at least one of an image and graphical user interface;
a main display configured to display an ultrasound image acquired with the ultrasound probe; and
a processor connected to the ultrasound probe, the touchscreen and the main display, wherein the processor is configured to:

display a plurality of steps of a workflow on the touchscreen, wherein the plurality of steps includes a first step and a second step;

graphically indicate the first step in the workflow;

display a first text instruction describing the first step in the workflow on the touchscreen at the same time as displaying the plurality of steps;

display a first pictogram graphically illustrating the first text instruction at the same time as displaying the first text instruction, wherein the processor is configured to display the first pictogram on at least one of the touchscreen or the main display, wherein the first pictogram comprises a representation of an M-mode tracing with a plurality of points marked on the representation of the M-mode tracing;

display an ultrasound image on the main display at the same time as displaying the plurality of steps on the touchscreen, the first text instruction on the touch screen, and the first pictogram on at least one of the touchscreen or the main display;

receive an input of a task described in the first text instruction;

determine that the workflow has not been completed after receiving the input;

graphically indicate the second step in the workflow after determining that the workflow has not been completed;

display a second text instruction describing the second step on the touchscreen after determining that the workflow has not been completed;

display a second pictogram graphically illustrating the second text instruction at the same time as displaying the second text instruction, wherein the second pictogram is displayed on at least one of the touchscreen or the main display; and display an updated ultrasound image on the main display at the same time as displaying the plurality of steps on the touchscreen, the second text instruction on the touchscreen, and the second pictogram on at least one of the touchscreen and the main display.

9. The ultrasound imaging system of claim 8, wherein the processor is configured to graphically indicate a current step in the workflow by highlighting one of the plurality of steps.

10. The ultrasound imaging system of claim 8, wherein the processor is further configured to graphically indicate that the first step has been completed after the input of the task described in the first text instruction has been received.

11. The ultrasound imaging system of claim 8, wherein the workflow comprises a cardiac workflow and wherein the processor is further configured to automatically calculate one or more cardiac parameters after the completion of the workflow.

12. The ultrasound imaging system of claim 10, wherein the processor is configured to graphically indicate that the first step has been completed by displaying a checkmark associated with the first step.

13. The ultrasound imaging system of claim 11, wherein the one or more cardiac parameters is selected from a list consisting of end diastolic diameter, end systolic diameter, fractional shortening, and sphericity.

* * * * *